United States Patent
Hamada et al.

(10) Patent No.: US 8,992,384 B2
(45) Date of Patent: Mar. 31, 2015

(54) TRAINING APPARATUS

(75) Inventors: Kazuyuki Hamada, Tokyo (JP);
Takeshi Akiba, Kanagawa (JP); Hiroshi Yokoi, Tokyo (JP)

(73) Assignee: System Instruments Co., Ltd, Tokyo (JP)

(*) Notice: Subject to any disclaimer, the term of this patent is extended or adjusted under 35 U.S.C. 154(b) by 154 days.

(21) Appl. No.: 13/643,252

(22) PCT Filed: Jun. 6, 2011

(86) PCT No.: PCT/JP2011/062969
§ 371 (c)(1),
(2), (4) Date: Oct. 24, 2012

(87) PCT Pub. No.: WO2012/168999
PCT Pub. Date: Dec. 13, 2012

(65) Prior Publication Data
US 2013/0137549 A1 May 30, 2013

(51) Int. Cl.
*A63B 24/00* (2006.01)
*G06K 9/00* (2006.01)

(52) U.S. Cl.
CPC ........ *A63B 24/0087* (2013.01); *G06K 9/00342* (2013.01); *Y10S 482/901* (2013.01)
USPC .............. 482/4; 482/1; 482/8; 482/901

(58) Field of Classification Search
USPC ............. 482/1–9, 900–902; 434/247
See application file for complete search history.

(56) References Cited

U.S. PATENT DOCUMENTS

| | | | |
|---|---|---|---|
| 7,280,871 B2 | 10/2007 | Davis et al. | |
| 7,658,695 B1* | 2/2010 | Amsbury et al. | 482/8 |
| 7,811,203 B2* | 10/2010 | Unuma et al. | 482/8 |
| 8,360,935 B2* | 1/2013 | Olsen et al. | 482/5 |
| 8,475,339 B2* | 7/2013 | Hwang et al. | 482/8 |
| 8,512,238 B2* | 8/2013 | Nissila et al. | 600/300 |
| 2011/0077128 A1 | 3/2011 | Hamada et al. | |

(Continued)

FOREIGN PATENT DOCUMENTS

| | | |
|---|---|---|
| JP | A-62-087156 | 4/1987 |
| JP | A-11-333021 | 7/1999 |
| JP | A-2001-204850 | 7/2001 |

(Continued)

OTHER PUBLICATIONS

Office Action issued in Japanese Application No. 2012-549584 dated Dec. 24, 2013 (with partial translation).
English-language Translation of International Preliminary Report on Patentability issued in International Application No. PCT/JP2011/062969 dated Dec. 10, 2013.

(Continued)

*Primary Examiner* — Glenn Richman
(74) *Attorney, Agent, or Firm* — Oliff PLC

(57) ABSTRACT

A training apparatus includes a training machine, a detecting unit, a signal generating unit, and a control unit. The training machine includes a displaceable part that is movable in response to exercise motions performed by the exerciser during training exercise. The detecting unit detects the displacement of the displaceable part or detects the displacement of the target training area of the exerciser resulting from the exercise motions. The signal generating unit generates a stimulus signal to be applied to the exerciser during the training exercise. The control unit corrects a content of processing relating to stimulus signal performed by the signal generating unit based on the displacement detected by the detecting unit.

9 Claims, 6 Drawing Sheets

(56) References Cited

U.S. PATENT DOCUMENTS

2011/0166488 A1  7/2011  Miyake
2012/0142497 A1* 6/2012  Ishii et al. .................. 482/4

FOREIGN PATENT DOCUMENTS

| JP | A-2004-209040 | 7/2004 |
| JP | A-2006-102156 | 4/2006 |
| JP | A-2006-192258 | 7/2006 |
| JP | A-2006-288622 | 10/2006 |
| JP | A-2006-296468 | 11/2006 |
| JP | A-2008-067917 | 3/2008 |
| JP | A-2008-206932 | 9/2008 |
| JP | A-2009-045236 | 3/2009 |
| JP | A-2009-119011 | 6/2009 |
| JP | A-2010-264320 | 11/2010 |
| JP | A-2011-067319 | 4/2011 |

OTHER PUBLICATIONS

Yokoi et al., "Development of Reflex Electric Stimulation Device for Assisting Walk," *Brain and Nerve*, Nov. 2010 (With English-language Abstract).
International Search Report issued in Application No. PCT/JP2011/062969; Dated Sep. 6, 2011 (With Translation).
Jan. 29, 2014 Office Action issued in Korean Patent Application No. 10-2012-7030323 9 (with partial English translation).
Aug. 13, 2014 Office Action issued in Taiwanese Patent Application No. 101110724 (with partial English Translation).
Sep. 24, 2014 Office Action issued in Japanese Patent Application No. 2012-549584 (with partial English Translation).
Jun. 25, 2014 Office Action issued in Chinese Patent Application No. 201180039651.6 (with English translation).

* cited by examiner

US 8,992,384 B2

TRAINING APPARATUS

TECHNICAL FIELD

The present invention relates to training apparatuses and particularly to those that utilize stimulus signals.

BACKGROUND ART

Various training apparatuses are known, one example of which is disclosed in JP-A-2009-45236. Often, various training apparatuses (or training machines) are used during training exercise depending on the intended purposes. People conduct training exercises in various situations, and they do so to achieve various objectives. Healthy people and athletes do exercises to build their muscle. Some do exercises so that they will not need homecare when they get old, while others do exercises as post-illness rehabilitation.

Training apparatuses are used to increase the effects of the training people conduct; accordingly, it is preferred that they have functions suitable for the intended purposes or actual training situation. In strength training, for example, it is preferred that the load applied to the target training area of the exerciser be fine-adjusted on an as-needed basis. The training apparatus of the above conventional art, for instance, which uses weights to allow the user to strengthen his or her muscle, has achieved the increased convenience of changing the weights by improving weight change functionality.

Recent years have seen the development of walk assist systems for those with difficulty walking due to cranial nerve paralysis or the like, and advances have been made in the study of muscle activation using electric stimuli and in such fields as brain-machine interfaces (BMI) and neuro-rehabilitation. One example of a related technical document is "Development of Reflex Electric Stimulation Device for Assisting Walk" written by Hiroshi Yokoi, et al. (BRAIN and NERVE-advances in the study of nerves, special topic in the November 2010 issue, vol. 62, No. 11 "Walking and Associated Abnormalities"). Even if research findings in such fields are put into practical use, the recovery of a physically impaired person enough to perform daily activities requires training exercises in which to practice walking and other actions to perform them accurately or smoothly to some extent or to restore the muscles required for those actions.

PRIOR ART LITERATURE

Patent Documents

Patent Document 1: JP-A-2009-45236
Patent Document 2: JP-A-2011-67319

Non-Patent Documents

Non-Patent Document 1: Hiroshi Yokoi at al. "Development of a Reflex Electrical Stimulation Device to Assist Walking" BRAIN and NERVE-advance in the study of nerves, special topic in the November 2010 issue, Vol. 62 No. 11 "Walking and Associated Abnormalities"

SUMMARY OF THE INVENTION

Technical Problem

The present inventors have conceived the technical idea that, during training exercise, a stimulus signal can be applied to the target exercise area of the exerciser. The term 'training' as used hereinafter is meant to include various training exercises such as rehabilitation exercises for the elderly or those done after an illness.

The stimulus signal is a signal of a particular intensity (a particular voltage in the case of an electric signal) or of a particular frequency applied to the exerciser (training apparatus user) to impart a particular stimulus. Application of the stimulus signal to the exerciser stimulates the body (diseased area) of the exerciser. Thus, by generating and applying stimulus signals in an appropriate manner, the training effect can be enhanced. In the case of rehabilitation or the like, training exercises lead to the restoration and maintenance or the like of muscles of the exerciser while stimulus signals help the rehabilitation.

Nevertheless, during a training exercise involving the use of stimulus signals, application of the same, single stimulus signal, irrespective of exercise motions or the like, may not allow appropriate measures to be taken if the stimulus signals do not fit the actual unique case of the exerciser (e.g., the content, progress, or effect of the training or the characteristics or disease condition of the exerciser) from the beginning or if the exerciser's situation may change afterward. This makes it difficult to achieve the desired training effects.

The present invention has been made to address the above issue, and an object of the invention is to provide a training apparatus suitable for training exercises involving the use of stimulus signals.

Solution to Problem

To achieve the above-mentioned purpose, a first aspect of the present invention is a training apparatus including a training machine, a detecting unit, a signal generating unit, and a control unit. The training machine includes a displaceable part that is movable in response to exercise motions performed by the exerciser during training exercise. The detecting unit detects the displacement of the displaceable part or detects the displacement of the target training area of the exerciser resulting from the exercise motions. The signal generating unit generates a stimulus signal to be applied to the exerciser during the training exercise. The control unit corrects a content of processing relating to stimulus signal performed by the signal generating unit based on the displacement detected by the detecting unit.

A second aspect of the present invention is the training apparatus of the first aspect, wherein the stimulus signal is a signal designed to stimulate a particular part of a brain activated to perform the motion during training exercise.

A third aspect of the present invention is the training apparatus of the first or the second aspect, further including a storage unit. The storage unit stores a plurality of different stimulus signals or stores stimulus parameters, the stimulus parameters designed as conditions of stimulus signals for generating a plurality of different stimulus signals. The control unit determines a stimulus signal to be applied to the exerciser based on the displacement detected by the detecting unit, the stimulus signal is determined from among the plurality of stimulus signals stored on the storage unit or a plurality of of stimulus signals generable from the stimulus parameters.

A fourth aspect of the present invention is the training apparatus of any one of the first to third aspects, wherein the control unit includes an evaluating unit and a comparative corrector. The evaluating unit evaluates the training exercise based on the displacement detected by the detecting unit and given reference information. The comparative corrector corrects, based on a result obtained by the evaluating unit, a content of processing relating to generation of stimulus signal performed by the signal generating unit.

A fifth aspect of the present invention is the training apparatus of the fourth aspect, wherein the reference information includes at least one selected from a group of distance of a displacement caused by exercise motion, duration of the training exercise, displacement velocity, smoothness degree of a displacement caused during the training exercise, symmetry degree of a displacement caused by each reciprocal exercise motion, a trajectory of a displacement caused by exercise motion, and acceleration of exercise motion.

A sixth aspect of the present invention is the training apparatus of any one of the first to fifth aspects, further including a load adjusting unit. The load adjusting unit adjusts a load applied to the displaceable part of the training machine. The control unit includes a load control unit. The load control unit corrects, based on the displacement detected by the detecting unit, a content of processing relating to the load performed by the load adjusting unit.

To achieve the above-mentioned purpose, a seventh aspect of the present invention is a training apparatus including detecting means, stimulating means, and correcting means. The detecting means detects a displacement of a training machine resulting from a motion during training exercise or detects a displacement of a target training area of an exerciser resulting from the motion during training exercise. The stimulating means applys a stimulus signal to the exerciser during the training exercise. The correcting means corrects a content of the stimulus signal based on the displacement detected by the detecting means.

Advantages of the Invention

In accordance with the first aspect of the invention, it is possible to feed back the result of the actual exercise motions performed by the exerciser during the training exercise to stimulus signal generation processing. This makes it possible to provide a training apparatus suitable for training exercises involving the use of stimulus signals, in which apparatus the result of the motions performed by the exerciser can be fed back to the generation of stimulus signals.

In accordance with the second aspect of the invention, the use of the "stimulus signal designed to stimulate a particular part of the brain activated to perform the training mortion" allows the exerciser to properly conduct the strength training required by "rehabilitation for the recovery of the movement functions of physically challenged persons with movement disorders resulting from damage to the nerve system" while allowing the exercise motions performed by the exerciser to be fed back to stimulus signal generation.

In accordance with the third aspect of the invention, the storage unit stores the information necessary to generate stimulus signals, and one stimulus signal is selected from the stored information based on the detection result obtained by the detecting unit.

In accordance with the fourth aspect of the invention, the training exercise is evaluated based on given reference information, and based on the evaluation result, stimulus signal generation is corrected.

In accordance with the fifth aspect of the invention, the actual exercise motions can be evaluated based on at least one of the following indices representing the exercise motions: the distance of the displacement caused by the exercise motions; the duration of the training exercise; the velocity of the displacement; the smoothness degree of the displacement caused during the training exercise; the symmetry degree of the displacement caused by each reciprocal exercise motion; the trajectory of the displacement caused by the exercise motions; and the acceleration of the exercise motions.

In accordance with the sixth aspect of the invention, the actual exercise motions performed by the exerciser during the training exercise can be fed back so that not only stimulus signals but also the load can be adjusted.

In accordance with the seventh aspect of the invention, it is possible to provide a training apparatus suitable for training exercises involving the use of stimulus signals, in which apparatus the result of the motions performed by the exerciser during the training exercise can be fed back to the generation of stimulus signals.

MODE FOR CARRYING OUT THE INVENTION

Embodiment.
[Apparatus Configuration According to an Embodiment ]

Figure 1:
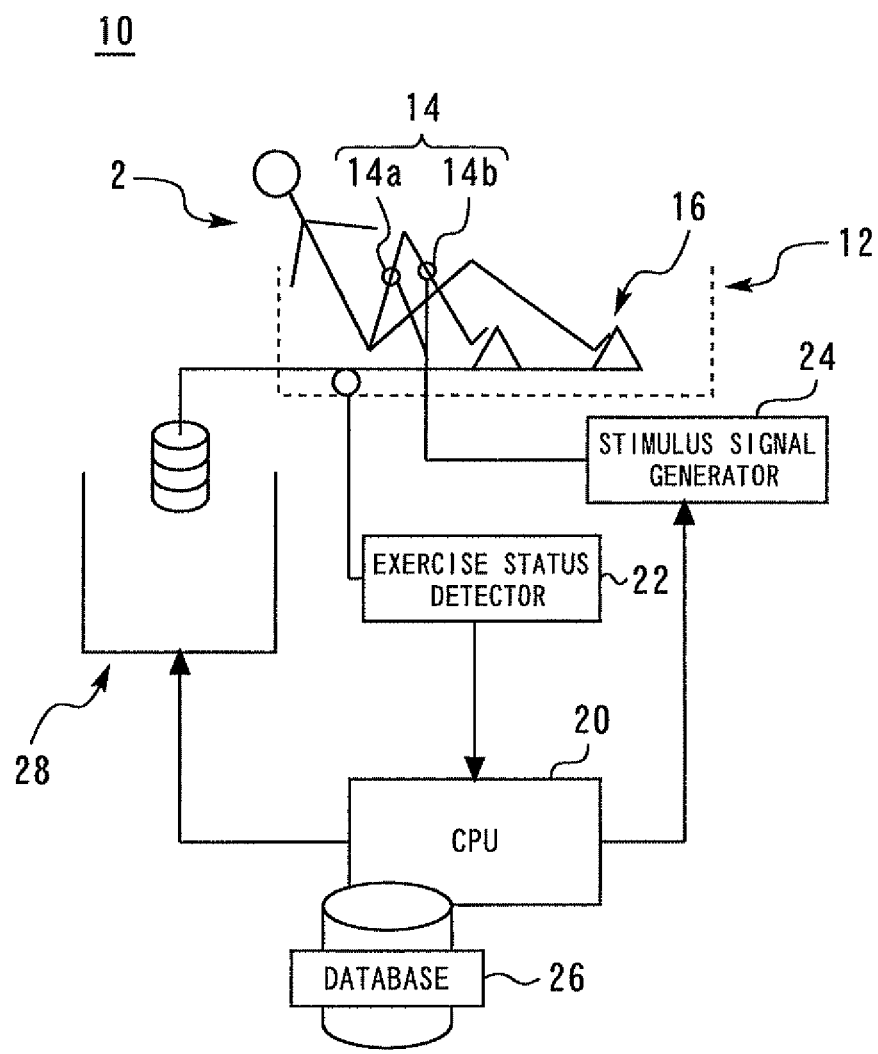
FIG. 1 illustrates the configuration of a training apparatus according to an embodiment of the invention.

FIG. 1 illustrates the configuration of a training apparatus 10 according to an embodiment of the invention. FIG. 1 also depicts a user 2 performing training exercise. The training apparatus 10 according to the present embodiment includes a strength training machine 12. The strength training machine 12, which can be used for a leg press, has a movable part 16 on which the user 2 places his or her feet during leg press. The leg press is an exercise in which the exerciser extends his or her legs; it strengthens the whole leg muscles, thereby improving the muscles necessary for basic actions such as standing up, walking, and sitting down.

The training apparatus 10 also includes a CPU (central processing unit) 20. The CPU 20 is connected to the following components: an exercise status detector 22, a stimulus signal generator 24, a training weight change apparatus 28, and a database 26.

While the user 2 is performing training exercise with the strength training machine 12, the exercise status detector 22 detects the status of the exercise. For that purpose, the training machine 12 includes a sensor for detecting the position of the movable part 16. Receiving an electric signal form this sensor, the exercise status detector 22 obtains information regarding the motion of the movable part 16 (e.g., its position, displacement, and displacement velocity along an axis that runs from left to right in FIG. 1). The exercise status detector 22 can be the "exercise situation detector" disclosed in JP-A-2011-67319.

The stimulus signal generator 24 is connected to stimulus electrodes 14 (14a and 14b, to be precise). In the present embodiment, the stimulus electrodes 14 are attached to the legs (thighs and calves) of the user 2, as illustrated in FIG. 1. A stimulus signal generated by the stimulus signal generator 24 is applied through these stimulus electrodes 14 to the legs of the user 2. The stimulus signal generator 24 is capable of generating an electric signal of the voltage and frequency specified by the data on the database 26 and of outputting that signal to the stimulus electrodes 14.

The database 26 stores stimulus signal parameters, which are used as the conditions for causing the stimulus signal generator 24 to generate different stimulus signals. These stimulus signal parameters include amplitudes, frequencies, burst frequencies, duty ratios, carrier frequencies, and patterns and are stored in the form of a database. A burst frequency is the frequency of a burst wave, which is a signal for activating the part of the brain that governs a particular motion. A carrier frequency is the frequency of a carrier wave, which is a dataless signal with only a carrier. A carrier signal is made up of a square wave of a frequency higher than that of a burst signal. Those burst and carrier waves are superimposed to form a stimulus signal, and its stimulus strength can be adjusted by the duty ratio. The training weight change apparatus 28 is capable of receiving, as input values, information regarding the stimulus signal parameters stored on the database 26 and outputting stimulus signals of different voltages and frequencies to the stimulus electrodes 14 based on those input values. The generation of stimulus signals by the stimulus signal generator 24 and the data stored on the database 26 will later be described in detail.

The training weight change apparatus 28 is deigned to adjust the weight the user 2 pushes while the leg press is being performed with the strength training machine 12 (i.e., adjust the load that works to prevent the displacement of the movable part 16 during the exercise). The training weight change apparatus 28 includes multiple weights, which may be equal or different in weight value. To achieve the load specified by a control signal from the CPU 20, the training weight change apparatus 28 combines some of those weights in accordance with the weight selection pattern predetermined according to the specified load. This allows the CPU 20 to automatically adjust the load without requiring the user 2 or an assistant to do so. It is preferred that the training weight change apparatus 28 be the "load imparting apparatus" disclosed in JP-A-2009-45236.

[Apparatus Operation According to the Embodiment]

Next described is the operation (controlled operation) of the training apparatus 10 of the present embodiment. The training apparatus 10 depicted in FIG. 1 achieves the following operations as discussed in the following subsections (1) to (3).

(1) Stimulus signals for activating the brain according to the embodiment

In the present embodiment, the stimulus signal generator 24 generates stimulus signals so that the signals can be used to stimulate the muscles of the user 2 through the nerves and brain to trigger a motion. In other words, for those with difficulty performing the motions required for daily activities due to cranial nerve paralysis, or paralysis resulting from a disease of the sensory motor system, or damage to the central nerve system, the present embodiment uses, as stimulus signals, electric signals applied to the nerves associated with the specific part of the brain to be activated, thereby activating that part of the brain to cause the associated joints to move. The stimulus signal parameters used as the conditions for generating stimulus signals are determined in advance with the use of the later-described "stimulus signal generating technique" and stored on the database 26. The CPU 20 controls the stimulus signal generator 24 and instructs the stimulus signal generator 24 to generate stimulus signals based on the stimulus signal parameters stored on the database 26 and to output those signals to the stimulus electrodes 14. The signals stimulate the nerves, brain, and muscles and assist exercise motions.

(2) Stimulus Signal Control Based on the Exercise Status

Figure 2:
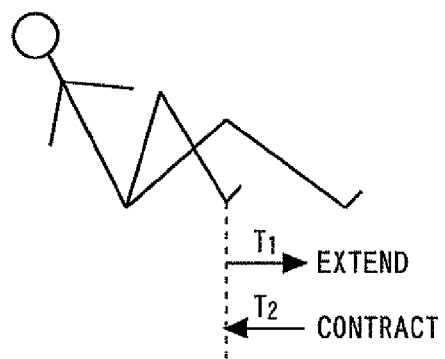
FIG. 2 is a diagram to illustrate the technique of the present embodiment for controlling stimulus signals based on the status of the exercise.
Figure 3:
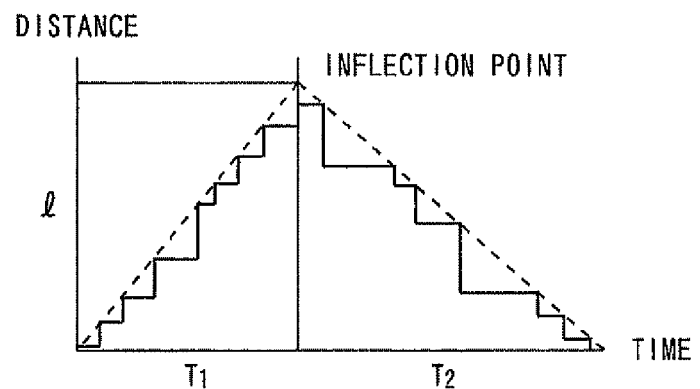
FIG. 3 is a diagram to illustrate the technique of the present embodiment for controlling stimulus signals based on the status of the exercise.
Figure 4:
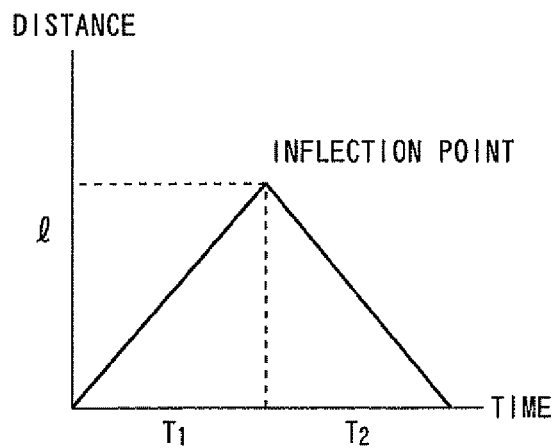
FIG. 4 is a diagram to illustrate the technique of the present embodiment for controlling stimulus signals based on the status of the exercise.

FIGS. 2 to 4 are diagrams to illustrate the technique of the present embodiment for controlling stimulus signals based on the status of the exercise. As stated above, the training apparatus 10 is a leg press machine. As illustrated in FIG. 2, the user 2 of the training apparatus 10 repeats the motions of leg extension (time $T_1$) and contraction (time $T_2$).

FIG. 3 is a graph illustrating the relationship between the distance l along which the user 2 moves his legs and time, as detected by the exercise status detector 22. FIG. 4 is a graph obtained when the ideal (smooth) leg motions are achieved. FIGS. 3 and 4 are illustrated so as to represent a relationship between distance l and time detected by the exercise status detector 22, and both which are based on the assumption that the user 2 is receiving stimulus signals and attempting to move his legs by his own will. The exercise status detection by the exercise status detector 22 results in FIG. 3, where during time $T_1$, the distance l increases up to its peak (inflection point) at which the user 2 has extended his legs to the fullest and then decreases during the time period from the time of the inflection point (i.e., the timing at which the user starts to contract the legs) to the end of time $T_2$. As shown by the dashed line of FIG. 3, when a physically unimpaired person performs the leg press, the distance l is expected to linearly increase up to the peak during time $T_1$ and then linearly decrease during the time period between the inflection point to the end of time $T_2$. However, when the user 2 has physical difficulty performing the leg press, such linear characteristics may not be obtained; the user 2 may suffer from cranial nerve paralysis, or paralysis resulting from a disease of the sensory motor system, or a movement disorder due to damage to the central nerve system. In such cases, the distance l would increase and decrease in a stepped manner, as shown by the solid line of FIG. 3. The difference between the dashed line and the solid line lies in the smoothness of the distance change.

The training apparatus 10 of the present embodiment is designed such that when the exercise status detector 22 detects such exercise status as shown in FIG. 3, the CPU 20 feeds back the detection result to the stimulus signal generator 24 to correct the generation of stimulus signals so that the stepped distance change becomes smoother. In other words, the CPU 20 overwrites the stimulus signal parameters that were used by the stimulus signal generator 24 at the time of the status detection with other parameters more desirable than those stored on the database 26 (i.e., with parameters that lead to the ideal leg motion). By this control being repeated several times, it will eventually become possible to select, among the stimulus signal parameters stored on the database 26, those parameters that allow generation of optimal stimulus signals suitable for the specific, unique condition of the user 2. This brings the motion of the user 2 closer to the ideal state of FIG. 4. As a result, appropriate measures can be taken during training involving the use of stimulus signals, even if the stimulus signals do not fit the actual case of the user (e.g., the content, progress, or effect of the training or the characteristics or disease condition of the user) from the beginning or even if the user's situation may change afterward.

The inflection point to be detected for the detection of the exercise status can be automatically detected by, for example, identifying the timing at which the distance 1 starts to decrease after an increase of the distance 1 or can be set in advance based on given conditions. The training apparatus 10 is also designed such that the CPU 20 corrects, based on the detection of the exercise status, the generation of stimulus signals by the stimulus signal generator 24 so that not only does the motion status become smoother, but also the distance 1 reaches a particular value.

The desirable motion can have one or more of the characteristics listed below. To achieve one or more of those characteristics, the CPU 20 corrects, based on the detected exercise status, the generation of stimulus signals by the stimulus signal generator 24. Specifically, the CPU 20 selects the stimulus signal parameters that lead to the selected one or more characteristics. For instance, the parameters that smooth the leg motion are set on a preferential basis, or the parameters leading to the longest motion distance are set on a preferential basis.

1) Smooth motion
2) The motion distance is long
3) Symmetrical (the symmetry between the increasing slope and the decreasing slope with respect to the inflection point as in FIG. 3)
4) The load gradually increases starting from zero
5) Motion times T1 and T2 are short (swift motion)

In the case of rehabilitation, the user 2 should not perform training exercise by applying a load to his body from the beginning. At first, the user 2 can use the training apparatus 10 with no load applied, so that one or more of the above target characteristics 1), 2), 3), and 5) can be achieved (i.e., until the user 2 can perform the motion that satisfies the characteristic(s) he selected). Thereafter, a load can be applied to examine whether he can still perform the target motion with the load applied. Load increase may be done gradually by repeating the load increase and the achievement of the target motion. It should be noted that the judgment as to whether the motion distance is long or not can be made based simply on the duration of one training exercise if there is found to be any correlation between the motion distance and the exercise duration.

(3) Load Increase According to an Exercise Menu

With the training apparatus 10 of the present embodiment, strength training exercise involving the use of stimulus signals can be performed according to a predefined program. The above-described "stimulus signal control based on the exercise status" causes the CPU 20 to select optimal stimulus signals (optimal stimulus signal parameters) so that the desirable motion characteristics (e.g., smoothness) can be satisfied for the motion of the user 2 performing exercise with the training apparatus 10. Once the user's motion becomes better due to such parameter optimization, the load is increased to strengthen the muscles of the user 2. In fact, even if the stimulation of the brain, nerves, and muscles of a physically impaired person with stimulus signals has made that person capable of performing exercise or walking, a certain level of muscle strength to perform daily activities is still necessary. If exercise has not long been performed due to physical impairment, well-planned training is necessary to fully restore and strengthen the weakened muscles.

Therefore, as already stated, the training apparatus 10 includes the training weight change apparatus 28 and allows the CPU 20 to increase the load applied by the training weight change apparatus 28 based on the exercise status detected by the exercise status detector 22. To increase the load in an appropriate manner, the load is increased gradually according to an exercise menu prepared in advance. This exercise menu can be created based, for example, on the comprehensive geriatric training (CGT) method devised at the Tokyo Metropolitan Institute of Gerontology.

In accordance with the training apparatus 10 of the present embodiment that achieves the above-described operations (1) to (3), it is possible to feed back the actual motions performed by the user 2 during training exercise to the generation of stimulus signals. Thereby, the actual motions of the user 2 can be reflected on the stimulus signals.

[Stimulus signal generating technique]

Figure 5:
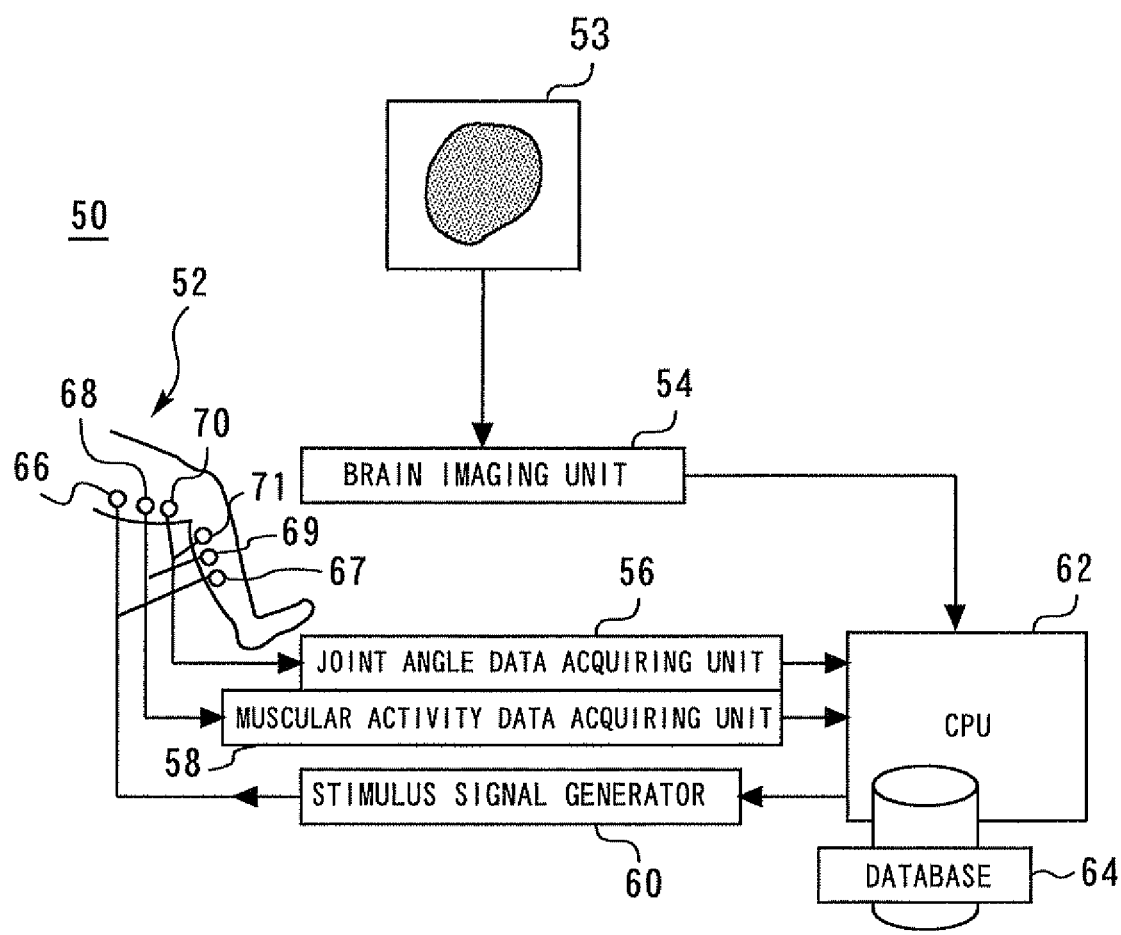
FIG. 5 is a diagram to illustrate the technique for generating stimulus signals according to an embodiment of the invention.

FIG. 5 is a diagram to illustrate the technique for generating stimulus signals according to an embodiment of the invention. FIG. 5 illustrates a stimulus signal generating system 50 according to the embodiment. This stimulus signal generating system 50 and the technique described below are used to acquire stimulus signal parameters, and the acquired parameters are stored on the database 26. The stimulus signal generator 24 receives, as input values, information regarding the stimulus signal parameters stored on the database 26 and outputs stimulus signals to the stimulus electrodes 14 based on those input values.

The stimulus signal generating system 50 includes the following components: a brain imaging unit 54; a joint angle data acquiring unit 56; a muscular activity data acquiring unit 58; a stimulus signal generator 60; and a CPU (central processing unit) 62 connected to these components. Further, angle sensors 70 and 71, muscle potential sensors 68 and 69, and stimulus electrodes 66 and 67 are attached to the legs 52 (legs of the subject).

The joint angle data acquiring unit 56 is connected to the angle sensors 70 and 71. The angle sensors 70 and 71 are acceleration sensors, and the joint angle data acquiring unit 56 calculates the joint angles of the legs 52 based on the detected acceleration of the motion of the legs 52. Likewise, the muscular activity data acquiring unit 58 acquires muscular activity data from the output values of the muscle potential sensors 68 and 69.

The brain imaging unit 54 is a device to measure the activation of the brain and acquires image data 53 (a pictorial representation of the brain activation) through, for example, an MRI (magnetic resonance imaging) device, an electroencephalograph, or a near-infrared spectroscopic device. In the present embodiment, various brain activation measuring devices (not illustrated) such as an MRI device and the like are arranged to measure the brain activation of the subject with the legs 52. The brain imaging unit 54 is connected to such devices so that the image data 53 schematically depicted in FIG. 5 can be acquired with the brain imaging unit 54.

The stimulus signal generator 60 is designed to generate stimulus signals, and particular methods are employed to acquire the positions of the nerves associated with the specific part of the brain to be activated, as well as a brain activation image, the joint angles, and the muscular activity data at that time. The CPU 62 is connected to a database 64, and once the information to be stored on the database 26 of FIG. 1 has been generated, it is stored on the database 64.

Figure 6:
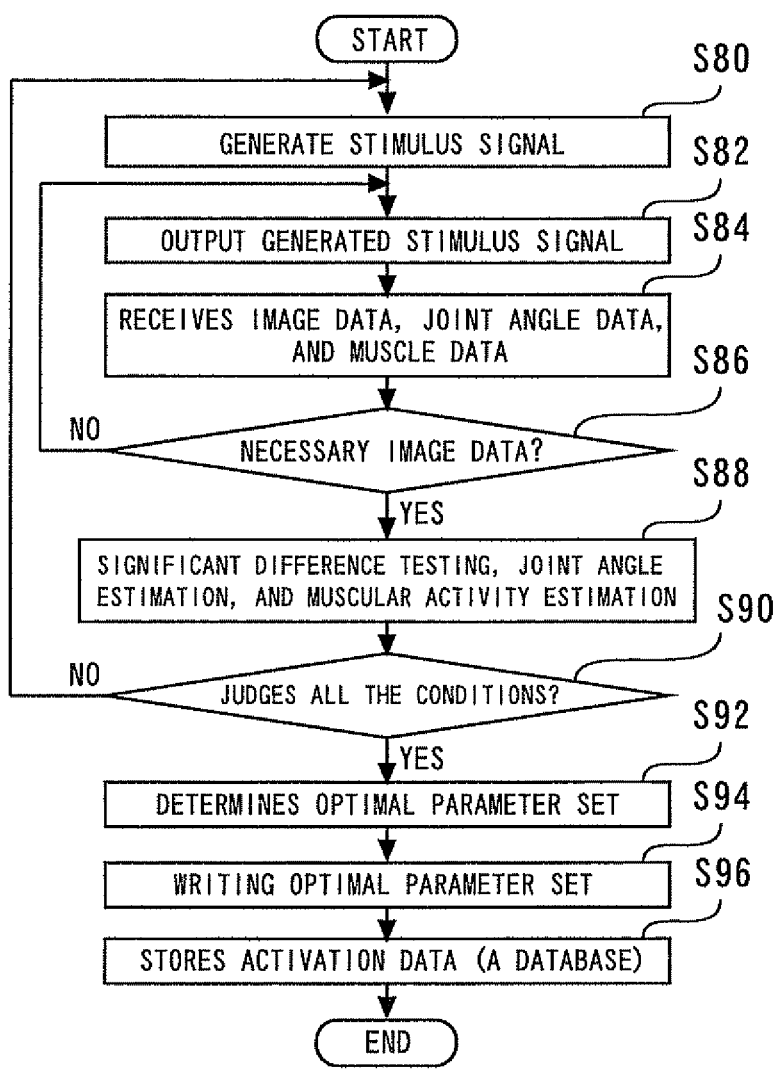
FIG. 6 is a flowchart illustrating the process of creating a database of stimulus signal parameters according to an embodiment of the present invention, which is the routine executed by the CPU.

FIG. 6 is a flowchart illustrating the process of creating a database of stimulus signal parameters according to an embodiment of the present invention. This flowchart is executed by the CPU 62. Prior to the execution, a list of multiple sets of stimulus signal parameters is created beforehand. To create a database of stimulus signal parameters, stimulus signal application to the subject and associated data collection are performed for each of those parameter sets created in advance, as will be described below. In the present embodiment, a database with multiple (e.g., 100) patterns of stimulus signal parameter sets ($P_1$ to $P_{100}$) is created so as to handle many different users and respond to many different situations or cases (different progress situations or different points in time of rehabilitation or training).

In the flowchart of FIG. 6, the CPU 62 first instructs the stimulus signal generator 60 to generate a stimulus signal based on a set of stimulus signal parameters (Step S80). In this step, one set of stimulus signal parameters is selected (the first parameter set on the list if Step S80 is executed for the first time; the nth parameter set on the list if Step S80 is executed for the nth time), and a stimulus signal is generated based on the selected parameter set.

Next, the CPU 62 executes the process of outputting the generated stimulus signal to the stimulus electrodes 66 and 67 (Step S82).

The CPU 62 then receives image data, joint angle data, and muscle data (muscular activity data) (Step S84). In this step, the CPU 62 receives, as input values, various data obtained by the brain imaging unit 54, the joint angle data acquiring unit 56, and the muscular activity data acquiring unit 58 in accordance with the output of the stimulus signal.

The CPU 62 then judges whether necessary image data has been obtained or not (Step S86). The image data 53 is the data obtained by the brain imaging unit 54, and it is used as pictorial information to identify brain activation. The judgment of Step S86 is the judgment as to whether the number of acquired images has reached the number required for the significant difference testing performed in the next step.

In Step S88, the CPU 62 performs significant difference testing, joint angle estimation, and muscular activity estimation. Ideally, when a stimulus signal has been applied to the user to assist his leg motion, the image data 53 obtained with that stimulus signal is preferred to show that only the particular part of the brain associated with leg motion has been activated (i.e., that part of the brain has exhibited the highest activation level). In other words, when a stimulus signal has been applied to the user to assist his leg motion, the image data 53 obtained with that stimulus signal is not preferred to show that any other part of the brain has also been activated (has exhibited a high activation level). Thus, in Step S88, the CPU 62 judges, using a significant difference testing method, whether only the particular part of the brain to be activated has been activated or not. The significant difference testing method may be any one of known methods including T-tests and Z-tests.

Next, in Step S90, the CPU 62 judges whether all the conditions have been satisfied, that is, whether each set of stimulus signal parameters has been used to perform Steps S80 through 88. If not, the routine returns to Step S80, and Steps 80 through 88 are performed for the rest of the conditions.

When all the conditions have been satisfied in Step S90, the CPU 62 determines an optimal parameter set (Step S92). In this step, the CPU 62 determines, as the optimal parameter set, a stimulus signal parameter set that has exhibited a higher value in the significant difference testing of Step S88 (a higher T-value in the case of a T-test).

Next, the CPU 62 performs the writing of the optimal parameter set (Step S94). The optimal parameter set obtained in Step S92 is written onto the database 64. This step is followed by Step S96 in which the CPU 62 stores the activation data in the form of a database. The thus created data including the optimal stimulus signal parameter set can be copied onto the database 26 (or a storage device) of the training apparatus 10 on an as-needed basis.

[Specific Operations Performed According To An Embodiment]

Figure 7:
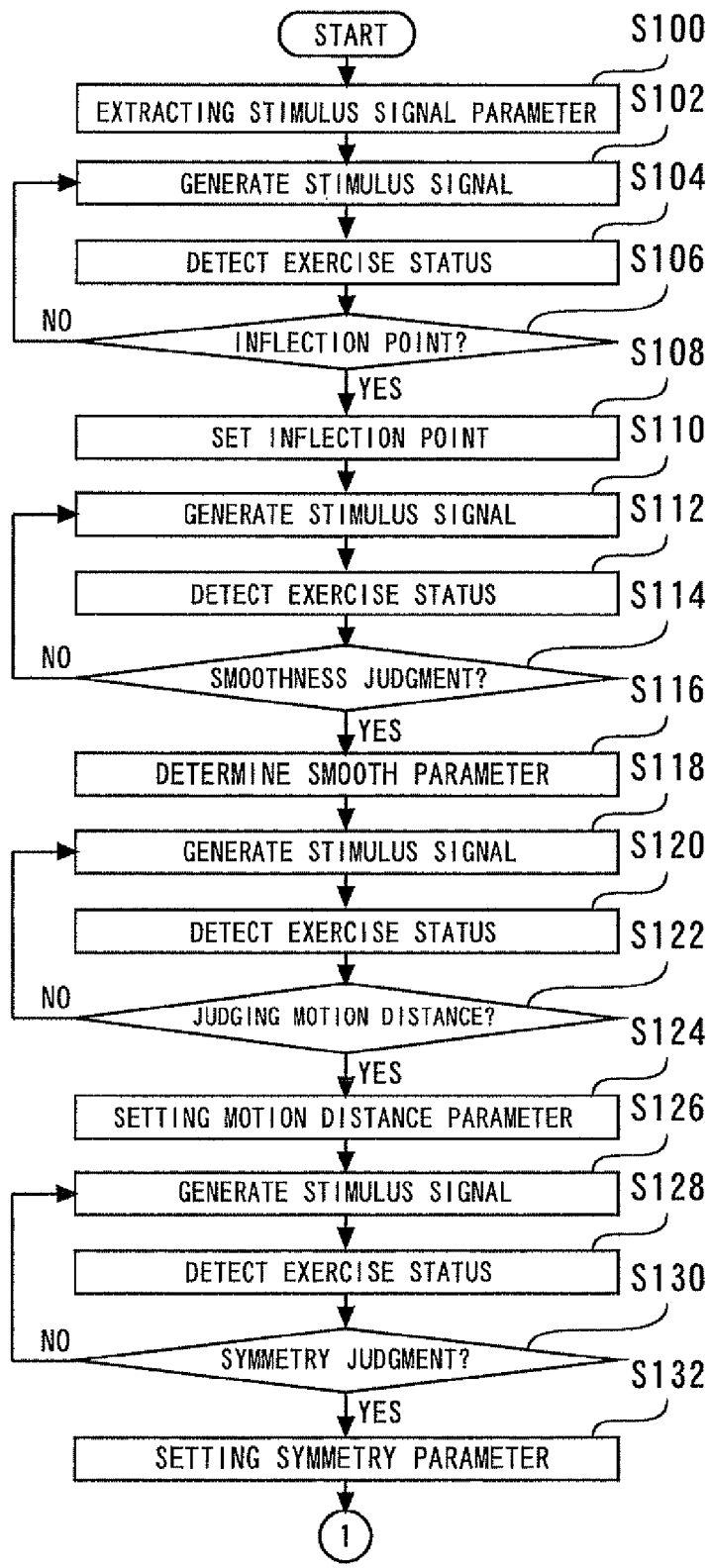
FIG. 7 is a flowchart illustrating the routine executed by the CPU of the training apparatus according to an embodiment of the invention.
Figure 8:
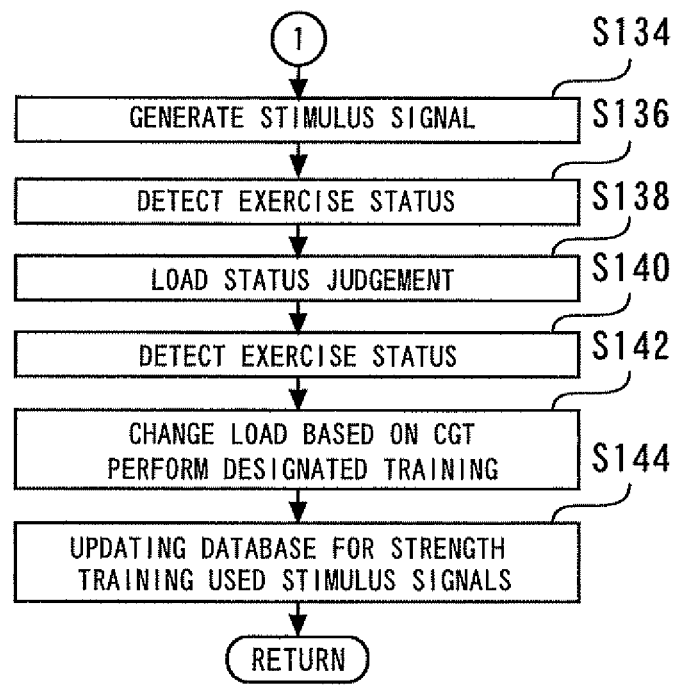
FIG. 8 is a flowchart illustrating the routine executed by the CPU of the training apparatus according to an embodiment of the invention.

FIGS. 7 and 8 are flowcharts illustrating the routine executed by the CPU 20 of the training apparatus 10 according to an embodiment of the invention.

The routine shown in FIGS. 7 and 8 starts with Step S100 in which the CPU 20 executes a process of extracting stimulus signal parameter data from the database 26.

The CPU 20 then executes a process of instructing the stimulus signal generator 24 to generate a stimulus signal (Step S102) and also executes a process of instructing the exercise status detector 22 to detect the exercise status (Step S104).

Next, the CPU 20 executes a process of judging, based on the detected exercise status, whether the training motion has reached the inflection point (see FIG. 3) (Step S108).

If so, the CPU 20 executes a process of setting that leg position as the inflection point (Step S106). With this step, the inflection point such as the one shown in FIG. 3 can be identified; thus, times $T_1$ and $T_2$ can also be identified.

Thereafter, the CPU 20 executes a process of instructing the stimulus signal generator 24 to generate a stimulus signal (Step S110) and also executes a process of instructing the exercise status detector 22 to detect the exercise status (Step S112).

Next, the CPU 20 executes a process of performing a smoothness judgment, that is, judges whether the exercise status detected in Step S112 represents a smooth motion (Step S114). Specifically, the CPU 20 execute a judgement process of judging whether the steps resulting from a non-smooth leg motion, such as the ones shown by the solid line of FIG. 3, are small relative to a given criterion. This judgment can be made using various known methods. For instance, a judgment can be made as to whether the displacement of the vertex of each obtained step from a smooth reference line (the dashed line of FIG. 3) is smaller than a given value. The condition required by this step will not be met if the smoothness judgment cannot be made due to the inability of the current stimulus signal to sufficiently assist the motion of the user 2 or if the smoothness of the motion is smaller than a given value. In such cases, the routine returns to Step S110 as indicated by the "NO" sign, and the same operations are performed using different stimulus signal parameters.

In Step S116, the CPU 20 executes a process of determining the parameters that have resulted in a smooth leg motion. This step selects, based on the smoothness judgment performed, an optimal stimulus signal parameter set from among the parameters stored on the database 26 to achieve the smoothest leg motion. In other words, this step sets, based on the result of the smoothness judgment performed in Step S114, the stimulus signal parameter set that has resulted in the smoothest motion as the optimal parameter set.

The CPU 20 then executes a process of instructing the stimulus signal generator 24 to generate a stimulus signal (Step S118) and also executes a process of instructing the exercise status detector 22 to detect the exercise status (Step S120).

Next, the CPU 20 executes a process of judging the motion distance (Step S122). This judgment can be made by comparing the total distance along which the user 2 has extended and contracted his legs during one set of training exercise against a given criterion (e.g., the same user's past training records). The condition required by this step will not be met if the motion distance judgment cannot be made due to the inability of the current stimulus signal to sufficiently assist the motion of the user 2 or if the motion distance is not larger than a given value. In such cases, the routine returns to Step S118 as indicated by the "NO" sign, and the same operations are performed using different stimulus signal parameters.

When the condition required by Step S122 has been met (indicated by the "YES" sign), the CPU 20 executes a process of setting motion distance parameters (Step S124). This step sets, based on the result of the motion distance judgment in Step S122, the stimulus signal parameter set that has resulted in the longest motion distance as an optimal parameter set.

The CPU 20 then executes a process of instructing the stimulus signal generator 24 to generate a stimulus signal (Step S126) and also executes a process of instructing the exercise status detector 22 to detect the exercise status (Step S128).

Next, the CPU 20 executes a process of performing a symmetry judgment (Step S130). The Step S130 is judgement processing to judge whether the training motion (displacement) satisfies a symmetrical characteristic with respect to its inflection point in the time-distance characteristic (see FIG. 3) obtained by the exercise status detector 22. To do so, the detection result obtained during time $T_1$ can be compared with the detection result obtained during $T_2$, which comes after the inflection point, and a judgment can then be made as to whether the difference between the two is larger than a reference value. The condition required by this step will not be met if the symmetry judgment cannot be made due to the inability of the current stimulus signal to sufficiently assist the motion of the user 2 or if the degree of the symmetry is smaller than a given value. In such cases, the routine returns to Step S126 as indicated by the "NO" sign, and the same operations are performed using different stimulus signal parameters.

In Step S132, the CPU 20 executes a process of determining symmetry parameters. In this step, based on the result of the symmetry judgment performed in Step S126, setting processing is executed for setting the stimulus signal parameter set that has resulted in the highest symmetry degree as an optimal parameter set.

The flowchart of FIG. 7 continues to FIG. 8, and the CPU 20 executes a process of instructing the stimulus signal generator 24 to generate a stimulus signal in Step S134 and also executes a process of instructing the exercise status detector 22 to detect the exercise status in Step S136.

Next, the CPU 20 executes a process of performing a load status judgment in Step S138 and executes a process of instructing the exercise status detector 22 to detect the exercise status in Step S140.

The CPU 20 then executes a process of changing the load based on a CGT (comprehensive geriatric training) theory and executes the process of allowing the user to perform designated training (Step S142). In this step, the load is changed in accordance with the "CGT-based exercise menu" stored on the database 26 (or a storage device), which menu is created in advance for multiple users of the training apparatus 10. Specifically, the CPU 20 controls the training weight change apparatus 28 such that the "load specified by the exercise menu" can be achieved.

After the load change, the CPU 20 judges whether or not the user 2 has been able to properly perform the training (leg press) with the changed load and stores the result as history data. If the user 2 has not been able to perform the traning, the fact that "the user has failed with the changed load" is recorded as the history data, and the routine proceeds to the next step.

Finally, the CPU 20 executes a process of updating the database for the strength training that has used stimulus signals (Step S144). In this step, the information stored on the database 26 is updated based on the result of the routine performed this time (e.g., the setup values for stimulus signal parameters, change history, load size, exercise motion history, detected exercise status history, and so forth, for each user). The routine then ends and returns to the start.

In accordance with the above routine, the actual motion of the user 2 during training exercise can be fed back to the stimulus signal processing at the CPU 20 and the stimulus signal generator 24 (i.e., to the values of stimulus signal parameters). Thus, the training apparatus 10 of the invention is capable of reflecting the motion of the user 2 on stimulus signals and suitable for training involving the use of stimulus signals.

Since such feedback control allows the detection result of the actual exercise status to be automatically reflected on stimulus signal parameters and load control, this reduces the burden on those who are engaged in specialized work, such as doctors, nurses, and physical therapists, during training exercise (especially during rehabilitation).

The following should be noted. The strength training machine 12, the exercise status detector 22, the stimulus signal generator 24, and the CPU 20 of the above-described embodiments correspond respectively to the "training machine," the "detecting unit," the "signal generating unit," and the "control unit" of the first aspect of the invention. The database 26 of the above-described embodiments corresponds to the "storage unit" of the third aspect of the invention. In the above-described embodiments, the values used for the judgments of Steps S114, S122, and S130 to achieve the desired target motions correspond to the "given reference information" of the fourth aspect of the invention. The training weight change apparatus 28 of the above-described embodiments corresponds to the "load adjusting unit" of the sixth aspect of the invention. The "detecting means" of the seventh aspect of the invention is implemented by the CPU 20 executing Steps S104, S112, S120, S128, and S136 of FIGS. 7 and 8. The "stimulating means" of the seventh aspect of the invention is implemented by the CPU 20 executing Steps S102, S110, S118, S126, and S134 of FIGS. 7 and 8. The "correcting means" of the seventh aspect of the invention is implemented by the CPU 20 executing Steps S116, S124, and S132 of FIGS. 7 and 8.

In the above-described embodiments, a stimulus signal is generated by the stimulus signal generating system 50 generating, based on a created database, an electric signal, which is applied to the nerves associated with the specific part of the brain to be activated, in order to activate that part of the brain and cause the associated joint to move. The present invention, however, is not limited only to the stimulus signal generating technique using the stimulus signal generating system 50. Instead, stimulus signal generating techniques other than the one adopted by the above-described embodiments may be used to generate a signal that stimulates or assists the exercise motion of the user (i.e., an electric signal of a particular voltage, frequency, duty ratio, etc.) and create a database, and the device generating that signal as a stimulus signal may be used in place of the stimulus signal generator 24. In such a case, the database 26 may store a data table specifying the conditions for generating different stimulus signals, and as in the above-described embodiments, the CPU 20 can be allowed to switch the signals.

While the above-described embodiments have adopted the leg press as the training exercise to be performed with the training apparatus 10, the invention is not limited thereto. The invention is also applicable to training apparatuses with which to perform, for example, hip abduction, rowing, and leg extension exercises. The invention is further applicable to training apparatuses for various training exercises to strengthen muscles of the upper body or for training exercises to move various body parts (e.g., arms, shoulders, elbows, wrists, fingers, or other upper-body or lower-body parts) as rehabilitation to recover from a limb movement disorder resulting from cranial nerve paralysis or a disease of the sensory motor system. In such training exercises as well, similar to the above description of the embodiment, the following operations: generation and application of stimulus signals, control of the stimulus signals based on the exercise status, and load increase based on the exercise menu may be implemented in the hardware system of FIG. 1 including the CPU 20, the training machine 10, the exercise status detector 22, the stimulus signal generator 24, the database 26, and the training weight change apparatus 28. In other words, what should be done is to create a database with the use of a stimulus signal generating technique, detect the exercise status for each training exercise, and evaluate the difference from the desirable target motion, thereby correcting (or giving "feedback" to) the CPU's control of stimulus signal generation and load adjustment based on the evaluation result. As to sensors used for detection of the user's motion, various sensing technologies can be employed; examples include those used to detect physical quantities such as positions, displacement, velocity, acceleration, angular velocity, and angular acceleration as electrical, mechanical, or other physical information. For the smoothness judgment or the symmetry judgment, for instance, acceleration sensors can be used.

As to the detection of the exercise status, it is possible to detect the displacement of a displaceable part of the strength training machine 12 that moves during training exercise. Alternatively, it is also possible to detect the displacement of the target training area of the exerciser (the user 2) resulting from exercise motion (as in the above-described embodiments, the leg angles or the lengths of the extended legs can be detected).

To detect the exercise status, the acceleration of exercise motion can be detected using acceleration sensors. Specifically, the acceleration detection can be done by attaching acceleration sensors to the body parts that move during the exercise (e.g., arms, shoulders, elbows, wrists, fingers, or other upper-body or lower-body parts). Alternatively, it is also possible to use a motion sensor to detect the displacement trajectory of exercise motion (e.g., a two-dimensional trajectory, that is, a trajectory in a plane, or a three-dimensional trajectory, that is, a trajectory in a three-dimensional space). By comparing the data obtained from such detection against reference data (reference values or reference patterns), the difference between the actual exercise motion and a given target motion (the currently desired motion or a standard or ideal motion) can be calculated. The calculation result can then be used for the "stimulus signal control based on the exercise status."

The flowchart of FIGS. 7 and 8 has illustrated the sequential, serial execution of the following operations: the inflection point setup operation, smoothness judgment, motion distance judgment, symmetry judgment, load status judgment, CGT-based load adjustment, and database creation. The invention, however, is not limited to this. These operations may not necessarily be performed in the order shown in FIGS. 7 and 8, but can be performed in a different order. The invention is not limited to such serial execution as in FIGS. 7 and 8 either. Some of those operations can instead be performed in parallel.

REFERENCE SIGNS LIST 10 training apparatus
12 strength training machine
14,14a,14b electrode
16 movable part
22 exercise status detector
24 stimulus signal generator
26 database
28 training weight change apparatus
50 stimulus signal generating system
52 legs
53 image data
54 brain imaging unit
56 joint angle data acquiring unit
58 muscular activity data acquiring unit
60 stimulus signal generator
64 database
66,67 stimulus electrode
68,69 muscle potential sensors
70,71 angle sensor

The invention claimed is:

1. A training apparatus comprising:
a training machine including a displaceable part movable in response to a motion from an exerciser during training exercise;
a detecting unit that detects a displacement of the displaceable part or detects a displacement of a target training area of the exerciser resulting from the motion;
a signal generating unit that generates a stimulus signal to be applied to the exerciser during the training exercise; and
a control unit that corrects a content of processing relating to the stimulus signal generated by the signal generating unit based on the displacement detected by the detecting unit, wherein:
the control unit includes an evaluating unit that evaluates the training exercise based on the displacement detected by the detecting unit and given reference information, and
the given reference information, used by the evaluating unit, includes at least one selected from the group consisting of displacement velocity, smoothness degree of a displacement produced during the training exercise, and symmetry degree of a displacement produced by each reciprocal exercise motion.

2. The training apparatus of claim 1, wherein the stimulus signal is a signal designed to stimulate a particular part of a brain that when activated, causes the motion during the training exercise to be performed.

3. The training apparatus of claim 1, further comprising:
a storage unit that stores a plurality of different stimulus signals or stores stimulus parameters, the stimulus parameters being designed as conditions of stimulus signals for generating the plurality of different stimulus signals,
wherein the control unit determines a specific stimulus signal to be applied to the exerciser based on the displacement detected by the detecting unit, the specific stimulus signal being determined from among the plurality of different stimulus signals stored on the storage unit or a plurality of stimulus signals generable from the stimulus parameters.

4. The training apparatus of claim 1, wherein the control unit further includes a comparative corrector that corrects, based on a result obtained by the evaluating unit, a content of processing relating to the generation of the stimulus signal performed by the signal generating unit.

5. The training apparatus of claim 4, wherein the given reference information further includes at least one selected from the group consisting of distance of a displacement produced by the exercise motion, duration of the training exercise, a trajectory of a displacement produced by the exercise motion, and acceleration of the exercise motion.

6. The training apparatus of claim 1, further comprising:
a load adjusting unit that adjusts a load applied to the displaceable part of the training machine,
wherein the control unit includes a load control unit that corrects, based on the displacement detected by the detecting unit, a content of processing relating to the load performed by the load adjusting unit.

7. The training apparatus of claim 2, wherein
the signal generating unit generates the stimulus signal by generating a superimposed wave of a burst wave and a carrier wave,
the burst wave being a burst signal for activating a particular part of the brain that governs a particular motion, and
the carrier wave being a carrier signal made up of a wave of a frequency higher than that of the burst signal, and
the control unit corrects a burst frequency and a carrier frequency,
the burst frequency is a frequency of the burst wave and the carrier frequency is a frequency of the carrier wave.

8. The training apparatus of claim 3, wherein
the storage unit stores the stimulus parameters in a form of a database, the stimulus parameters being used as the conditions for causing the signal generating unit to generate the different stimulus signals,
the stimulus parameters including at least one of amplitudes, frequencies, burst frequencies, duty ratios, carrier frequencies, and patterns of the different stimulus signals,
the burst frequency being a frequency of a burst wave that is a burst signal for activating a particular part of a brain that governs a particular motion, and
the carrier frequency being a frequency of a carrier wave made up of a wave of a frequency higher than the burst frequency signal,
the signal generating unit generates the stimulus signal by superimposing the burst wave and the carrier wave to form the stimulus signal, and
the control unit sets the duty ratio so as to adjust stimulus strength of the stimulus signal.

9. The training apparatus of claim 4, wherein
the evaluating unit includes:
a comparing unit that compares the displacement detected by the detecting unit and the given reference information, and
a judgment unit that judges if the displacement detected by the detecting unit fulfills the given reference information based on a comparison result of the comparing unit, and
the comparative corrector includes:
a returning unit that performs, until the judgment unit judges that the displacement satisfies the given reference information, one or more operations of stimulus signal generation by the signal generating unit and displacement detection by the detecting unit in accordance with the stimulus signal performed by the stimulus signal generation, the returning unit using different stimulus parameters for each operation, and
a setting unit that executes setting processing for setting, as an optimal parameter set, a stimulus parameter set resulted in the highest degree in an evaluation by the evaluating unit.

* * * * *